United States Patent
Zschau

(10) Patent No.: US 8,477,996 B2
(45) Date of Patent: Jul. 2, 2013

(54) METHOD AND DEVICE FOR FINDING AND TRACKING PAIRS OF EYES

(75) Inventor: Enrico Zschau, Dresden (DE)

(73) Assignee: Seereal Technologies S.A., Munsbach (LU)

( * ) Notice: Subject to any disclaimer, the term of this patent is extended or adjusted under 35 U.S.C. 154(b) by 356 days.

(21) Appl. No.: 12/743,077

(22) PCT Filed: Nov. 12, 2008

(86) PCT No.: PCT/EP2008/065352
§ 371 (c)(1),
(2), (4) Date: Aug. 13, 2010

(87) PCT Pub. No.: WO2009/062945
PCT Pub. Date: May 22, 2009

(65) Prior Publication Data
US 2010/0303294 A1    Dec. 2, 2010

(30) Foreign Application Priority Data
Nov. 16, 2007 (DE) .......................... 10 2007 056 528

(51) Int. Cl.
*G06K 9/00* (2006.01)
(52) U.S. Cl.
USPC ........... 382/103; 382/115; 382/117; 382/118; 382/154; 382/171; 382/224
(58) Field of Classification Search
USPC ................. 382/103, 118, 154, 115, 117, 171, 382/224
See application file for complete search history.

(56) References Cited

U.S. PATENT DOCUMENTS

| | | | |
|---|---|---|---|
| 6,539,100 B1* | 3/2003 | Amir et al. | 382/117 |
| 7,835,568 B2* | 11/2010 | Park et al. | 382/154 |
| 7,950,802 B2* | 5/2011 | Schwerdtner et al. | 351/210 |
| 8,369,607 B2* | 2/2013 | Mashitani et al. | 382/154 |
| 2003/0086061 A1 | 5/2003 | Pfleger | |
| 2003/0156742 A1* | 8/2003 | Witt et al. | 382/118 |
| 2005/0063582 A1* | 3/2005 | Park et al. | 382/154 |
| 2005/0089212 A1* | 4/2005 | Mashitani et al. | 382/154 |
| 2005/0259873 A1* | 11/2005 | Sung et al. | 382/195 |
| 2007/0147671 A1* | 6/2007 | Di Vincenzo et al. | 382/128 |
| 2008/0231805 A1 | 9/2008 | Schwerdtner | |

FOREIGN PATENT DOCUMENTS

| | | |
|---|---|---|
| DE | 197 31 303 A1 | 2/1999 |
| DE | 10 2006 002 001 A1 | 7/2007 |
| EP | 0 350 957 A2 | 1/1990 |
| WO | WO 03/079902 A1 | 10/2003 |

(Continued)

OTHER PUBLICATIONS

Multimodal face—tracking, Wollhauf et al., IEEE,1-4244-0567-X, 2006, pp. 13-18.*

(Continued)

*Primary Examiner* — Jayesh A Patel
(74) *Attorney, Agent, or Firm* — Saul Ewing LLP

(57) ABSTRACT

A method for finding and subsequently tracking the 3-D coordinates of a pair of eyes in at least one face, including receiving image data, which contains a sequence of at least one digital video signal of at least one image sensor, finding eyes or tracking previously found eyes in the image data, ascertaining the 3-D coordinates of the found or tracked eyes, associating the found or tracked eyes with a pair of eyes and providing the 3-D coordinates of the pair of eyes.

26 Claims, 8 Drawing Sheets

FOREIGN PATENT DOCUMENTS

| | | |
|---|---|---|
| WO | WO 03079902 A1 * | 10/2003 |
| WO | WO 2007/019842 A2 | 2/2007 |
| WO | WO 2007019842 A2 * | 2/2007 |

OTHER PUBLICATIONS

International Search Report, dated Mar. 3, 2009, and Written Opinion, issued in priority International Application No. PCT/EP2008/065352.

Ji et al., "Real time 3D face pose discrimination based on active IR illumination," Pattern Recognition, 2002, Proceedings, 16th Intl. Conf., IEEE Comput. Soc. US, Bd. 4, Aug. 11, 2002, pp. 310-313, XP010613529.

Perez et al., "Face and eye tracking algorithm based on digital image processing," 2001 IEEE Intl. Conf. on Systems Man and Cybernetics, pp. 1178-1183 (Oct. 7, 2001) XP010569798.

Inostroza, P., "Real-time update of eye features on the 3D head model texture," Cyberworlds, 2003 Intl. Conf., pp. 259-264 (Dec. 3, 2003) XP010674972.

Kim et al., "A fast center of pupil detection algorithm for VOG-based eye movement tracking," Engineeringin Medicine and Biology Society, IEEE-EMBS 2005, pp. 3188-3191 (Jan. 2, 2005) XP031001262.

* cited by examiner

METHOD AND DEVICE FOR FINDING AND TRACKING PAIRS OF EYES

CROSS REFERENCE TO RELATED APPLICATIONS

This application claims the priority of PCT/EP2008/065352, filed on Nov. 12, 2008, which claims priority to German Application No. 10 2007 056528.5, filed Nov. 16, 2007, the entire contents of which are hereby incorporated in total by reference.

BACKGROUND OF THE INVENTION

The present invention relates to a contactless method for finding and subsequent tracking of the 3D coordinates of a pair of eyes in at least one face in real time.

In contrast for example to contact methods, contactless methods for finding and tracking faces do not require any additional means, such as head-mounted cameras or spots. The advantage of these contactless methods is that the freedom of movement of the subjects to be tracked is not restricted in any way by physical means and that the subjects are not bothered by the use of such means.

Contactless detection and tracking methods are known in the prior art. U.S. Pat. No. 6,539,100 B1 and EP 0 350 957 B1, for example, disclose how the viewing direction of an observer is detected with the help of certain face and eye characteristics which are extracted from the recorded images. While U.S. Pat. No. 6,539,100 B1 describes a method that serves to find out which object is being viewed by an observer, EP 0 350 957 B1 additionally has the target to track the movement of the eyes over a certain period of time.

DE 197 31 303 A1 discloses a method and device for contactless, headgear-less measurement of the viewing direction of eyes even where head and eye movements take place at a fast pace and in a large range. The eye is illuminated with infrared light, imaged by an optical system and recorded by at least one image sensor; and the thus generated image is subsequently processed by a viewing direction processor which can be configured by a main processor to determine the viewing direction by finding the position of the centre of the eye pupil and by determining the corneal reflections, and is then displayed on a monitor.

WO 03/079 902 A1 also describes a method of contactless detection and tracking of eyes at various lighting conditions in real time. The eyes are detected by executing the following steps: recording of two actively illuminated images, where one image represents the 'bright pupil effect' and the other image represents the 'dark pupil effect' of the eyes; creation of a differential image of these two images, where the resulting differential image only shows contrast at those positions where the contrast of the two images differs; marking out the contrast points in the differential image as possible eyes; and comparison of the possible eyes with pre-recorded images of eyes and non-eyes which serve as reference images in order to be able to distinguish eyes from non-eyes in the differential image with a high probability. The eyes are then tracked in an image that follows the detection by applying a Kalman filter and comparing the expected eye positions with eye positions that are actually detected in the differential image. If the comparison does not produce any results, the position of the eyes is determined in a further step with the help of a clustering algorithm, which clusters the possible eye positions based on their intensities in the image and which compares these clusters with the expected position.

This prior art method exhibits a number of disadvantages. On the one hand, the process of detecting and tracking the eyes takes advantage of an image which is created based on one image with 'bright pupil effect' and one with 'dark pupil effect' using an interlaced scanning method, where the two images are not recorded simultaneously by one image sensor, but one after another. A temporally non-coincident image recording in conjunction with a superposition of the images by the interlaced scanning method, which serves to reduce the amount of image data for transmission, does not allow a reliable detection and tracking of the eyes in real time. On the other hand, this method only allows to detect and to track eyes which are spatially very close to the image sensor, because the effects caused by the active illumination diminish as the distance of the eyes to the illumination source grows, which leads to the effect that the eyes to be detected can no longer be distinguished from other objects or a noise in the differential image.

WO2007/019842 tries to counteract these disadvantages in that the eye positions are found using a hierarchically organised routine, where the amount of data to be processed is gradually trimmed down, starting with the amount of data of the total video frame (VF) and proceeding to a target face region (GZ) and finally to a target eye region (AZ). In addition, each instance or group of instances is always executed on a dedicated computing unit, so that they run in parallel. However, WO2007/019842 does not explain how the eyes are found and tracked.

However, real-time detection and tracking of eyes is a decisive factor in human-machine interaction. It is thus particularly desired to provide methods for detecting and tracking eyes which make precise real-time finding and tracking of eyes possible.

Precise and efficient determining of the position also in the Z direction is necessary in particular in the context of dynamic applications, where large and fast movements of the faces in all spatial directions are possible. Such dynamic applications include for example autostereoscopic or holographic displays where the desired image impression will only occur if the eye positions of the observers are determined precisely both spatially and temporally, so that the autostereoscopic or holographic image information can be directed at the actual eye position. In contrast, in the stationary applications which are known in the prior art, such as devices for monitoring of drivers and pilots, the detection and tracking range is rather small, since in those applications the range of movement of the subjects is typically restricted to a minimum in all spatial directions.

The methods known in the prior art further exhibit the problem that the position information of the eyes cannot be delivered in real time, in particular not where more than one face is to be identified and tracked.

SUMMARY OF THE INVENTION

It is thus the object of the present invention to provide a method that allows to find and track reliably, precisely and efficiently the eye positions of one or multiple faces in all three spatial directions in a sufficiently large detection and tracking range in real time, while only causing a low computational load. It is in particular the object of the present invention to make possible the efficient and precise finding of at least one eye.

This object is solved according to this invention in that a method is proposed which comprises the following steps: reception of image data, which are supplied as a sequence of one or multiple video signals of at least one image sensor;

finding eyes or tracking already found eyes in the image data; determining the 3D coordinates of the found or tracked eyes; assignment of the found or tracked eyes to form pairs of eyes; and providing the 3D coordinates of the pairs of eyes.

In the preferred embodiment, the image data are received in the form of a video sequence which is recorded by at least one image sensor. The reception of the image data is alternatively also possible using other ways of transmission, for example in the form of single images.

The process step of finding eyes comprises the following steps: identification of one or multiple faces in the image data; determining the 3D coordinates of at least one identified face; definition of a first search area on the identified face; and finding at least one eye in that first search area. Various methods and devices for identifying faces in the images are known in the prior art, which shall be included completely by reference here, where the position information of the identified faces is typically output in the form of 2D coordinates. The Z coordinate to complete the 3D coordinates of the face position can here be found preferably by a stereo analysis of the image data received from two image sensors, as known from the prior art, or by any other known method, e.g. a distance measurement. Having determined the 3D information of the face, an area can be defined which includes at great probability at least one eye of the face by applying known models of eye positions on faces. Should none of the models be applicable on the identified face, the area in which the search for the eyes is performed can include the entire face. This area is understood and will be referred to below as the first search area for eyes, and the subsequent steps of finding eyes are all limited to this first search area. In the next step, at least one eye is found in the first search area. In the case that no eye is found it is assumed that no eye is detectable in the face in this image for example due to closed eyelids, and the eye is thus considered non-existing. In all other cases, the eye(s) found in each face are further processed in the subsequent process steps. Searching the eyes in a small search area typically brings about results much faster than searching in a search area which includes the entire face or even the entire image.

In a further process step, the 3D coordinates of the found eyes are determined. In a preferred embodiment, another stereo analysis is applied to achieve this, but any other known method of determining 3D coordinates of an object can alternatively be applied. Thereafter, the found eyes are assigned to form pairs of eyes, where either the distance between two eyes, which can be computed based on the 3D coordinates of the eyes, is compared with the known eye separation of a model pair of eyes, or where any other suitable assignment method is applied, for example the classification which is preferred here. It is preferable for further processing of the found eyes in the form of pairs of eyes to determine the 3D coordinates of the pairs of eyes, because the positions of the eyes and of the face can be found based on those data using known face-eye models, thus reducing the amount of data which are required for subsequent tracking of a once identified face.

Tracking already found pairs of eyes generally includes the steps of defining at least one second search area on the identified face and tracking the eyes of the pair of eyes in this search area. According to one aspect, a second search area is defined for each eye. The pairs of eyes which are determined in the step of finding eyes are here used as a starting point for further tracking. The areas in which the eyes of the investigated pair of eyes are tracked are defined based on the 3D coordinates of the eyes. The thus defined areas which are preferably smaller than the first search areas, are understood and referred to as second search areas for eye tracking. The thus defined tracking of pairs of eyes allows the definition of sufficiently small second search areas even if the eyes or the face move at fast pace or in a large range, which in turn makes it possible to track the pairs of eyes in real time.

Finding at least one eye further comprises the following steps: computing an expected size of a part of an eye depending on the distance of the identified face from the image data providing image sensor; computing a greyscale value as a threshold for a segmentation in the first search area depending on the distance of the identified face from the image data providing image sensor; pre-processing the first search area aiming to improve the contrast; segmentation of the first search area after that pre-processing; computing one or multiple combined regions in the segmented first search area, where the combined region is a collection of adjacent pixels with at least approximately identical greyscale value; determining a size of each computed combined region, and comparing the expected size of the part of the eye with the determined size of the combined region, where the combined region represents a found eye if the determined size of the combined region at least approximately corresponds with the expected size of the part of the eye. Hereby, the contrast in the image data is modified such that the relevant parts of the eye are more clearly distinguishable from other objects in the image data. Among other things, this makes it possible that eyes which are further away from the image data providing image sensor are nevertheless found when applying this method.

According to one aspect of the present invention, the pre-processing step includes a greyscale value histogram equalisation in the first search area.

According to another aspect of the present invention, the tracking of already found eyes further comprises the following steps: computing an expected size of a part of the eye depending on the distance of the identified face from the image data providing image sensor; determining a minimum greyscale value in the second search area; and iteration over a greyscale value as a threshold in the second search area, where the iteration is terminated when at least two eyes are detected. The iteration comprises the following steps: computing the greyscale value as a threshold for a segmentation in the second search area depending on the distance of the identified face from the image data providing image sensor, from the current iteration step, and from the minimum greyscale value; segmentation of the second search area; computing one or multiple combined regions in the segmented second search area, where the combined region is a collection of adjacent pixels with at least approximately identical greyscale value; determining a size of each computed combined region; and comparing the expected size of the part of the eye with the determined size of the combined region, where the combined region represents a tracked eye if the determined size of the combined region at least approximately corresponds with the expected size of the part of the eye. Thanks to these process steps it is possible that in particular more remotely situated eyes can be tracked in real time, and that more precise results are provided as regards the 3D coordinates of the eyes than would be possible with conventional methods.

According to another aspect of the present invention, the segmentation of the search areas is achieved with the help of an efficient method, such as a binarisation method. Further, according to a preferred embodiment, the assignment of eyes to form pairs of eyes is conducted by way of classification with a support vector machine, which determines based on similarities of given eyes and non-eyes to the found eyes which eyes belong to a pair of eyes. However, the assignment of eyes to form pairs of eyes shall not be restricted to a classification nor to the use of a support vector machine.

The present invention further relates to a computer programme which, if run on a computer, controls the same such to execute the method according to this invention.

The present invention further relates to a device for finding and subsequent tracking of the 3D coordinates of a pair of eyes in at least one face with means for receiving image data comprising a sequence of at least one digital video signal from at least one image sensor, means for finding eyes in the image data, means for tracking already found eyes in the image data, means for determining the 3D coordinates of the found or tracked eyes, means for the assignment of the found or tracked eyes to form pairs of eyes, and means for providing the 3D coordinates of the pair of eyes. The means for tracking already found eyes in the image data further include means for identifying one or multiple faces in the image data, means for determining the 3D coordinates of at least one identified face, means for defining a first search area on the identified face, and means for finding at least one eye in the first search area. The means for tracking already found eyes in the image data in particular include means for defining a second search area on the identified face and means for tracking the eyes of the pair of eyes in the second search area.

Further preferred aspects of the present invention are defined in the dependent claims.

BRIEF DESCRIPTION OF THE DRAWINGS

Preferred embodiments of the present invention will be explained below only for the purpose of illustration and without any limitation and in conjunction with the accompanying drawings, where.

DETAILED DESCRIPTION

Figure 1:
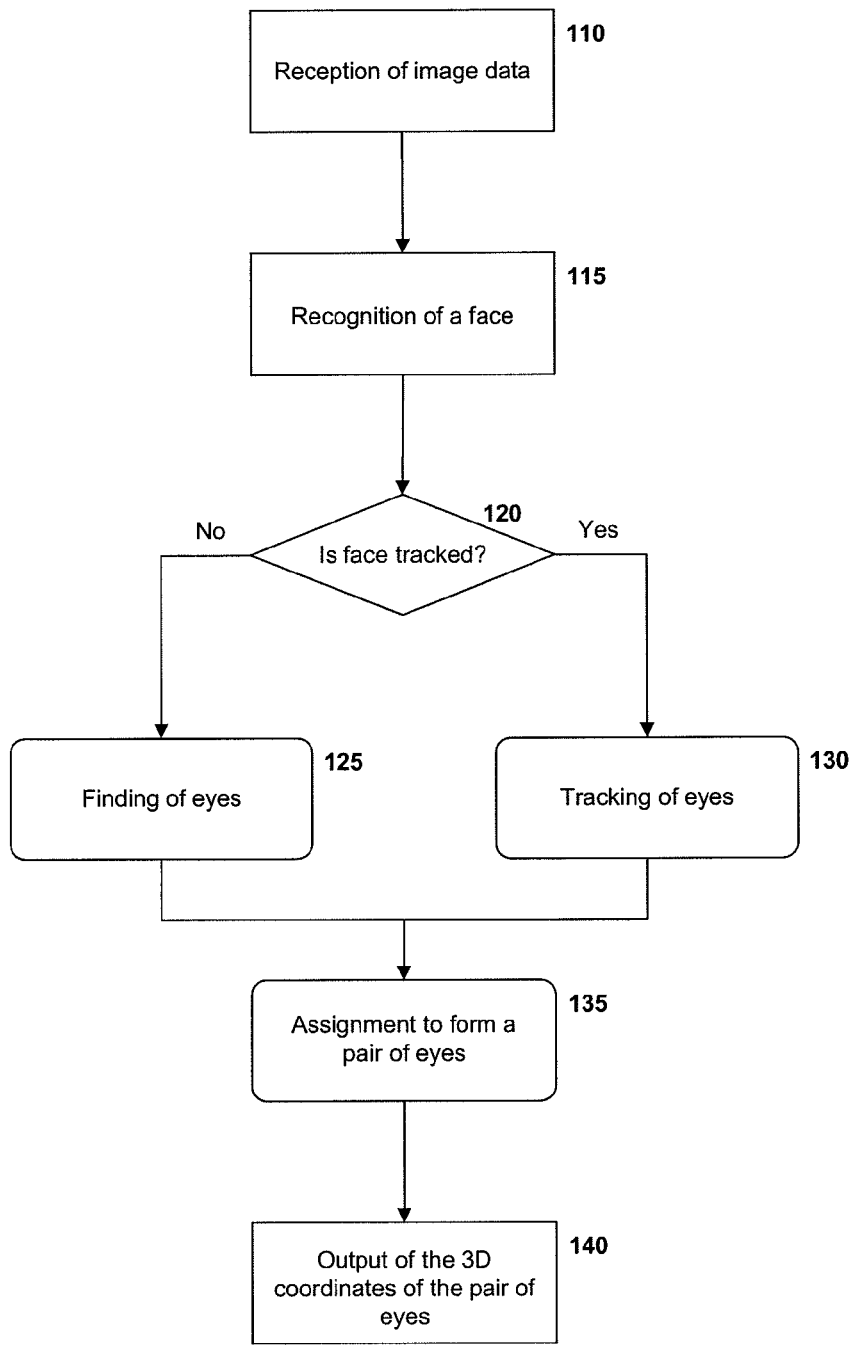
FIG. 1 shows a flowchart of a method according to this invention.

FIG. 1 shows a first embodiment of the method according to this invention, said method being capable of finding and tracking the eyes of up to four observers at a refresh rate of at least 25 Hz in real time. The method thus makes it possible to process up to four observers at a detection and tracking frequency of at least 25 images per second, or one observer at a detection and tracking frequency of for example 60 images per second. Image data, which are recorded by one or multiple image sensors and which are transmitted in the form of a video sequence through transmission means, such as a serial interface, are received in step 110. The image data which are recorded by the image sensor are illuminated by active lighting in the embodiment which is preferred here. The detection range of the image sensor is illuminated with light to enable the image sensor to record images. An illumination with infrared light is preferred here, which has a wavelength in a range of about 700-950 nm, preferably 850 nm, according to an embodiment of the present invention. The active illumination serves to highlight the eyes of the subjects in the image data.

The so-called 'dark pupil effect', where the pupil appears particularly dark in contrast to its environment, is created when the active illumination is arranged relatively far away from the optical axis of the image sensor. For the 'bright pupil effect', the active illumination is arranged close to the optical axis of the image sensor, so that, similar to the 'red-eye effect' in photography, the emitted light is reflected from the background of the eye and recorded by the image sensor.

The 'dark pupil effect' is the preferred effect according to one embodiment. Other effects, such as the 'bright pupil effect', which means that the pupil appears brighter than its environment, can also be taken advantage of in order to make the eyes or relevant parts of the eyes distinguishable from the environment.

The image sensors are designed such that, in conjunction with the active illumination, a detection and tracking of eyes is achieved with as little errors as possible in the following steps even if the eyes are situated at a large distance from the image sensor. The detection range is not limited by the method according to this invention, but by the image sensors used. In the embodiment which is preferred here, this detection range covers a distance of about 0.5 m to 3.5 m from the image sensors, depending on the image sensors actually used. However, larger detection ranges can also be achieved with the method according to this invention if suitable image sensors are used. The image data can be compressed by known methods for video data compression, or be available for further processing in the form of raw data.

The received image data are provided to the face identification step 115. Faces are identified taking advantage of prior art face detection methods. Faces are typically identified in the image data in step 115 with the help of a pattern recognition routine. Once a face has been identified, the coordinates that specify the spatial position of the face in relation to the image sensor are determined, preferably in the form of 3D coordinates. The origin of the coordinate system of the 3D coordinates is defined before the method is executed; in the preferred embodiment with one image sensor it is defined by the optical axis of the image sensor and the image sensor itself, and in an embodiment with two image sensors it is defined by the centre of a segment that connects the optical axes of the image sensors and the image sensors themselves. The 3D coordinates can be determined preferably by applying a stereo analysis of 2D images which are recorded by at least two image sensors. In the stereo analysis, the disparities of an identified face are found in the image data. The disparity is the distance of the coordinates of a pixel in the image data of a stereo image which is represented in the image data by detecting a point in space by at least two image sensors from different directions in the recorded image data with different coordinates, if the point is detected by both image sensors. The image sensors are measured to find a function which images the disparity of the pixels in the stereo image to the distance of the point in space in relation to the image data providing image sensor and vice versa. The distance from the image sensors is then determined by applying this function, and the Z coordinate of the 3D coordinates can thus be determined based on that distance. Alternatively, the Z coordinate can be determined using any other method that is known in the prior art.

It is further preferred that in one embodiment the distance of the face from the image data providing image sensor is determined based on the 3D coordinates. The distance of a face from the image sensor can also be determined using other methods, e.g. by way of distance measurement with a laser.

The identification of faces in the image data in step 115 is preferably executed in synchronism with the reception of the image data, so that the image data are searched for faces which have not yet been detected or which have been lost during tracking. It is thus provided in the preferred embodiment that already identified faces and their positions are stored. The preferred method is further designed such that the identification of new faces is executed independent of the eye tracking in step 130. If faces are identified in the image data, it is checked in step 120 whether or not those faces are already being tracked. This can be checked based on stored characteristics of the face, such as the eye separation or face proportions, or, preferably, based on the 3D coordinates. If the result of this check is that the identified face is not yet tracked, then the eyes or the pair of eyes of that face are not yet found. In this embodiment, eyes are found in the face in step 125 by defining at least one first search area on the identified face and by finding at least one eye in the defined search area. In the case that the face is already tracked, further tracking is executed by defining a second search area in which at least one eye of the pair of eyes of the face is tracked. In one embodiment, the first search area is preferably larger than the second search area. In the preferred embodiment, in steps 125 and 130 at least one eye is found in each first search area and then tracked in the second search area. The assignment of found or tracked eyes to form a pair of eyes in step 135 is preferably executed after having determined the coordinates, which are preferably 3D coordinates. The found or tracked pairs of eyes are provided for further processing, e.g. for a repeated execution of the method or for other applications, which are not part of the embodiment described here. The 3D coordinates of the pairs of eyes are provided in step 140 for example through a suitable interface 720 to be further processed by a computer 725, as will be described hereunder with reference to FIG. 7.

Figure 2:
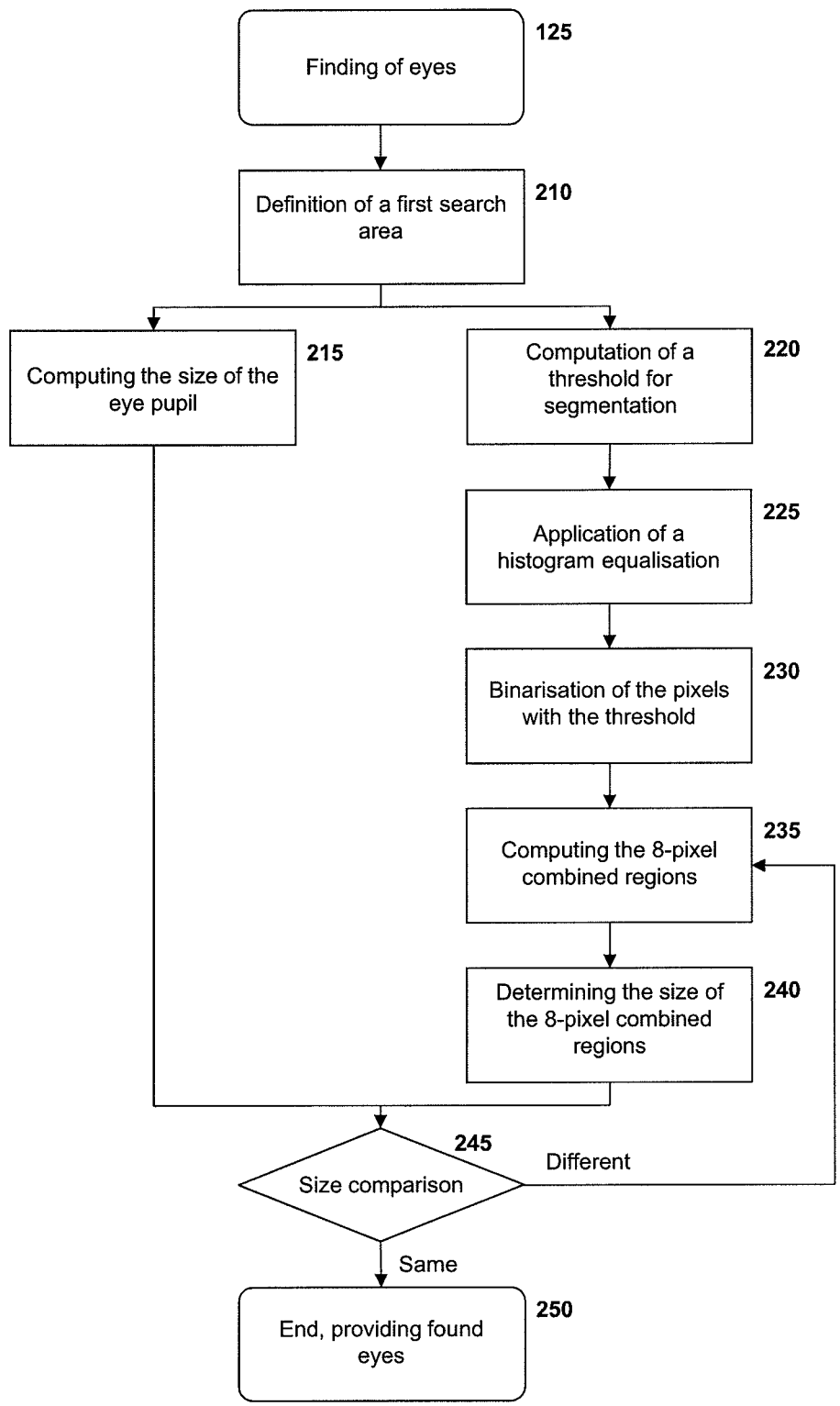
FIG. 2: shows a flowchart that illustrates the process of finding eyes according to an embodiment of this invention.
Figure 3:
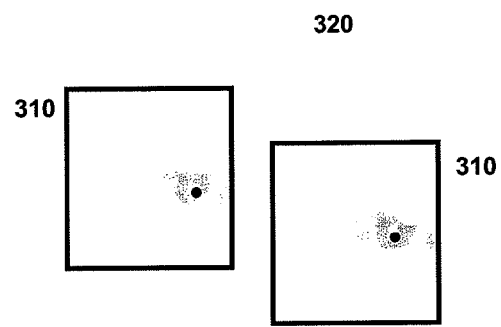
FIG. 3: shows image data with defined first search areas on a face according to an embodiment of this invention.

Other preferred embodiments of the method will be described with reference to FIG. 2 and FIG. 3. The process shown in FIG. 2 describes in detail the operations of finding eyes in step 125 in FIG. 1. The process will be started if it is found out that a face is not yet tracked, and that consequently no eyes have been found in that face. Eyes are found based on the current image data and 3D coordinates of the identified face. In process step 210, at least one first search area 310 is defined on the identified face, where the size of the first search area depends on the characteristics and accuracy of the selected face detection method. In a preferred embodiment, the first search area has a size of about 50 mm×50 mm. The first search area 310 is defined with the help of the determined 3D coordinates of the face and the face geometry. On the basis of this information, it can be computed in what region the eyes of this face are most likely located, so that the first search area(s) is/are defined in the image data based on that computed region. FIG. 3 shows defined first search areas 310 in an image 320, one for each eye in the face, said eye being specified with the help of the 'dark pupil effect'. The further process steps will be executed in the respective first search area only, which has the effect that the investigated regions on the face become much smaller, which in turn positively affects computational load and thus the efficiency of the method. Based on the distance of the face from the image data providing image sensor, the size of a part of the eye of the identified face is computed in step 215. In one embodiment, this part of the eye is the eye pupil, because it is highlighted with particular contrast to other parts of the eye when the 'dark pupil effect' is employed. In another embodiment, the iris is used as a relevant part of the eye in addition to the eye pupil. The distance can be computed based on the 3D coordinates of the identified face, or by any other method known in the prior art. Further, the distance value is preferably handed over to process step 125 for further usage. The expected size of the eye pupil is computed by applying adequate algorithms, which will not be described in more detail here. A further step of finding eyes comprises the computation of a threshold for a segmentation of the first search area in step 220.

A segmentation here is an image processing method where regions which are related as far as the content is concerned are created by combining adjacent pixels in accordance with a certain homogeneity criterion. In the preferred embodiment, the greyscale value is used as homogeneity criterion. In image processing, the greyscale value is the brightness or intensity value of an individual pixel. It must be noted here that the greyscale value is independent of the colour of the image data.

In a preferred embodiment, the image data include greyscale values ranging from white to black in 256 intermediate steps. A greyscale value is computed as a threshold to be used in subsequent process steps in dependence on the distance of the identified face from the image data providing image sensor. As brightness and intensity values are shifted in the image data as the distance from the image sensor changes, the threshold is preferably computed considering that distance. In a further step 225, the first search area is pre-processed such to distinguish the relevant parts of the image, such as eye pupils or eye pupils and iris, further from the other parts of the image.

In the embodiment which is preferred here, this pre-processing step includes a greyscale value histogram equalisation in the first search area. In a histogram equalisation, the statistic distribution of the greyscale values or colour values in the image data is transformed using an equalisation function in order to achieve a better distribution of greyscale values or colouring, thus improving the contrast and normalising the content of the image data within the search area. This serves to reduce the influence of different brightness in the image data, which result from the distance of the face from the image data providing image sensor and consequently from the reduced effect of the active illumination or from additional illumination effects, such as incident sunlight, which has a large proportion of infrared light, so to create similar contrast values for further processing.

Once the image data in the first search area are thus processed, a segmentation is performed in step 230. Any suitable methods can be used for this segmentation which allow an assignment of pixels based on their greyscale values. According to one embodiment, the preferred segmentation method is a binarisation of the pixels. The threshold that was computed in step 220 is used for this binarisation. The pixels in the first search area are given the value 1 if their greyscale values are below the threshold, and they are given the value 0 if their greyscale values are above the threshold. An inverse binarisation of the pixels, where the pixels are given the value 0 if their greyscale values are below the threshold, and the value 1 if their greyscale values are above the threshold, can be used as well. It is thus achieved that in the first search area only relevant pixels above the threshold are given the value 1, thus appearing black, and that all other pixels are given the value 0, thus appearing white. In a subsequent process step 235, combined regions are computed in the segmented search areas. A combined region is a region where adjacent pixels were found to belong together based on identical properties, for example as regards their greyscale values.

In a preferred embodiment, 8-pixel combined regions are computed, which represent the togetherness of the pixels better in singular cases than for example 4-pixel combined regions. All 8 pixels which are adjacent to one pixel are then considered, and it is computed whether these adjacent pixels have the same greyscale value. In the case of 4-pixel combined regions, only horizontally and vertically adjacent pixels are considered. All pixels which have the same greyscale value will be assigned to the same combined region. According to one embodiment, pixels which lie within a certain range of greyscale values are assigned to a common combined region.

In the subsequent step 240, the sizes of the computed combined regions are determined. The determined size of each computed combined region is then compared with the expected size of the pupil or part of the eye. If it is found out in the size comparison step 245 that the size of a combined region is about the same as the expected size of the eye pupil, it is concluded that the combined region is an eye. In all other cases, the combined region is no eye. It goes without saying that multiple eyes can thus be found in a first search area, which will be further processed in the process step 135 of the assignment to form a pair of eyes. According to this embodiment, the process steps of finding eyes end with step 250 providing the found eyes. If in the first search area no eye was found, the process is either repeated with a larger first search area, or it is terminated without detectable eyes in the identified face.

In another preferred embodiment, the threshold, the algorithms to compute the threshold, or the parameters of the algorithms to compute the threshold are found and optimised by measuring the detection performance in a large number of test patterns and test pattern sequences. In doing so, the distance of the face or of the eyes from the image data providing image sensor is considered, because for example the power and effect of the active illumination diminish as the distance to the image data providing image sensor grows. A practical algorithm to compute the threshold is:

Threshold=Min Brightness Value+Initial Value+(Max Distance−Distance)/100 where the Min Brightness Value is the lowest brightness of a pixel in the area to be segmented, the Initial Value is a value that is defined based on values determined during the above-mentioned optimisation measurements, the Max Distance is the maximum possible distance in mm of an observer from the image data providing image sensor, and the Distance is the actual distance in mm of the face or of the eyes from the image data providing image sensor.

Figure 4:
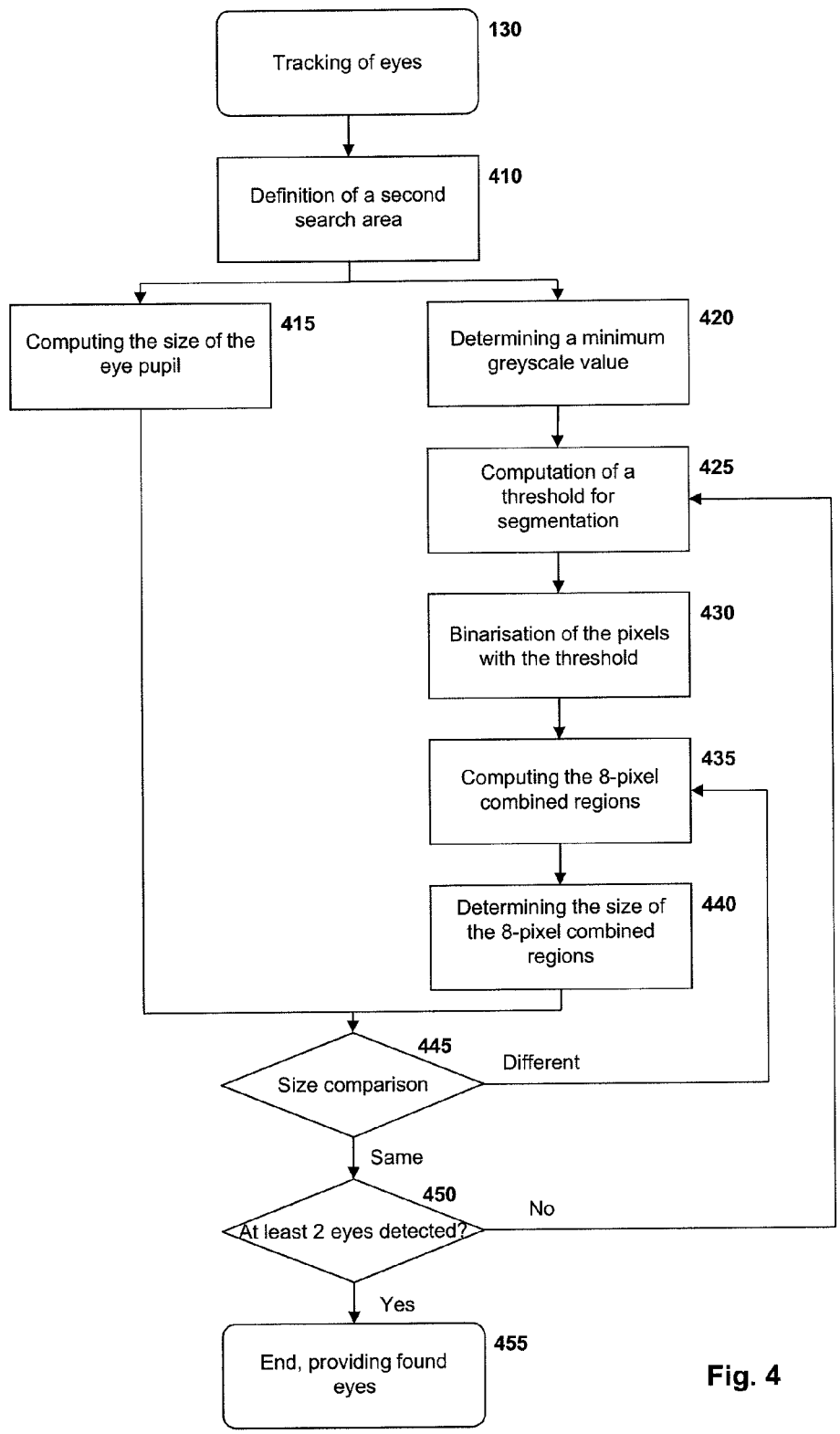
FIG. 4: shows a flowchart that illustrates the process of tracking already found eyes according to an embodiment of this invention.

Other preferred embodiments of the method will now be described with reference to FIG. 4 and FIG. 5. The method shown in FIG. 4 describes in detail the individual operations of tracking eyes in step 130 in FIG. 1. In contrast to the step of finding eyes, when tracking already found eyes the second search areas for tracking the eyes are defined in step 410 based on the known positions of the eyes. The second search areas are preferably defined to be smaller than the corresponding first search areas. The size of the second search area typically corresponds roughly with the size of an eye, where the size of the second search area can be enlarged dynamically depending on the refresh rate of the image data which are recorded by the image sensors, and on the freedom of movement and speed of movement of the eyes. In a further preferred embodiment, the second search area has a size of about 20 mm×15 mm, where it is assumed that the eye is completely covered by the search area. The second search areas 510 are defined on the face 320 as follows. When the process comes to process step 130 in FIG. 1, the 3D coordinates of the eyes to be tracked are already known from previously executed process steps, in particular step 140 of previous image data. It is for example determined based on multiple previous 3D coordinates of the eyes whether the found and tracked eyes carry out a relative movement in a certain direction at a certain speed. If this is confirmed, a forecast of the eye positions in the current image can be computed. For this, a number of methods are known in the prior art, which shall be included completely by reference here. The second search area is then defined accordingly in consideration of the forecast position of the eye. In the other cases that either no relative movement was detected or that the eyes were found the first time in the previous step, the second search area is defined based on the position of the eye found in the previous step 140.

Figure 5:
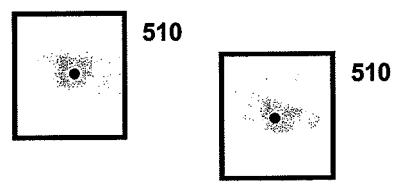
FIG. 5: shows image data with defined second search areas on a face according to an embodiment of this invention.

An exemplary definition of second search areas 510 on an already identified face 320 is shown in FIG. 5. When comparing those to the search areas 310 in FIG. 3, it can be seen clearly that the second search area 510 is much smaller, so that the computational load is minimised due to the smaller number of pixels in the second search area.

After having defined the second search area, the size of a part of an eye is computed depending on the distance of the eyes from the image data providing image sensor in step 415. The computation is for example executed as described in step 215 above. Subsequently, a minimum greyscale value is determined in the second search area in step 420. The minimum greyscale value is again determined with the help of image processing methods which are known in the prior art. The determined minimum greyscale value of step 420 is continued to be used in the following iteration. The iteration comprises the following steps: computing a greyscale value as the current threshold for a segmentation (step 425); segmentation of the search area (step 430); computing of combined regions (step 435); determining the sizes of the combined regions (step 440); and comparison of the determined sizes with the expected sizes (step 445). After having completed step 445, the iteration will be terminated in step 450 if at least two eyes were found. In all other cases, another iteration step will be conducted. In a preferred embodiment, the number of iteration steps is limited to four, irrespective of the number of eyes found in the comparison step, so that the iteration will be terminated after the fourth iteration step, thus only providing the eyes found so far. In each iteration step, first the greyscale value is determined, which is then used as threshold for the subsequent segmentation. The current threshold is determined with the help of known methods in consideration of the distance of the eyes from the image data providing image sensor, of the minimum greyscale value from step 425 and, of the current iteration step. In each iteration step, the threshold is further adjusted such that in the subsequent segmentation more regions in the image data are classified as potentially eye containing regions with the help of the threshold.

The process of eye tracking according to the just described embodiment ends with step 455 providing the trackable eyes.

A number of known segmentation methods can be employed, as already described above. In a preferred embodiment, the binarisation method is used as the image processing function. As described above, the pixels are given the value 0 if their greyscale values are below the threshold, and the value 1 if their greyscale values are above the threshold, or vice versa.

After the binarisation, combined regions are computed as described above. The 8-pixel combined region described above is the preferred type of combined region. Thereafter, the size of each combined region is determined. This determined size is then compared with the expected size of the part of the eye, e.g. the eye pupil as preferred here. If the expected size is about the same as the determined size, it is assumed that an eye has been found. This comparison is carried out for each computed combined region. When the sizes of all combined regions are compared with the expected size of the part of the eye, it will be determined how many eyes were found in that iteration step. If at least two eyes were found, the tracking of the eyes in the current image data will be terminated. The process according to FIG. 1 is then continued with the found eyes in step 135.

Advantageously, the iteration will also be terminated when for example four iteration steps have been conducted. Depending on the available computing resources, the iteration can alternatively be terminated after fewer or after considerably more iteration steps, if at least two eyes still have not been found.

The threshold for the segmentation in an iteration step is computed in accordance with the computing algorithm used in step 125 and with the parameters introduced there, the computation is advantageously carried out as follows:

Threshold=Min Brightness+Initial Value+Iteration Value+(Max Distance−Distance)/100 where the Iteration Value is a value which ranges from 0 to X with a step width of 1, and which represents the number of iteration steps that have already been conducted. The maximum number of iteration steps X can be determined by way of optimisation of the values found in the measurements described above. In the embodiment described here, the maximum number of iterations is four.

When tracking eyes in the second search area, it is thus possible that no eye is found even after completion of the defined maximum number of iteration steps. In such case the steps of tracking eyes are for example repeated in a larger second search area, or the steps of finding eyes are carried out anew.

According to one embodiment, when defining the second search area it is assumed that if the 3D coordinates of the pair of eyes have not or only minimally changed from finding in one image to tracking in a subsequent image then the 3D coordinates of that pair of eyes will again be (almost) identical in the image that follows that subsequent image. In contrast, in the case that the 3D coordinates of the tracked pair of eyes have moved away from the initial 3D coordinates when finding the eyes over a number of images, the 3D coordinates and thus the second search areas of the next image can generally be forecast with the help of a movement vector which is defined by the movement described above and the speed of the movement using known methods such as a Kalman filtering.

Figure 6:
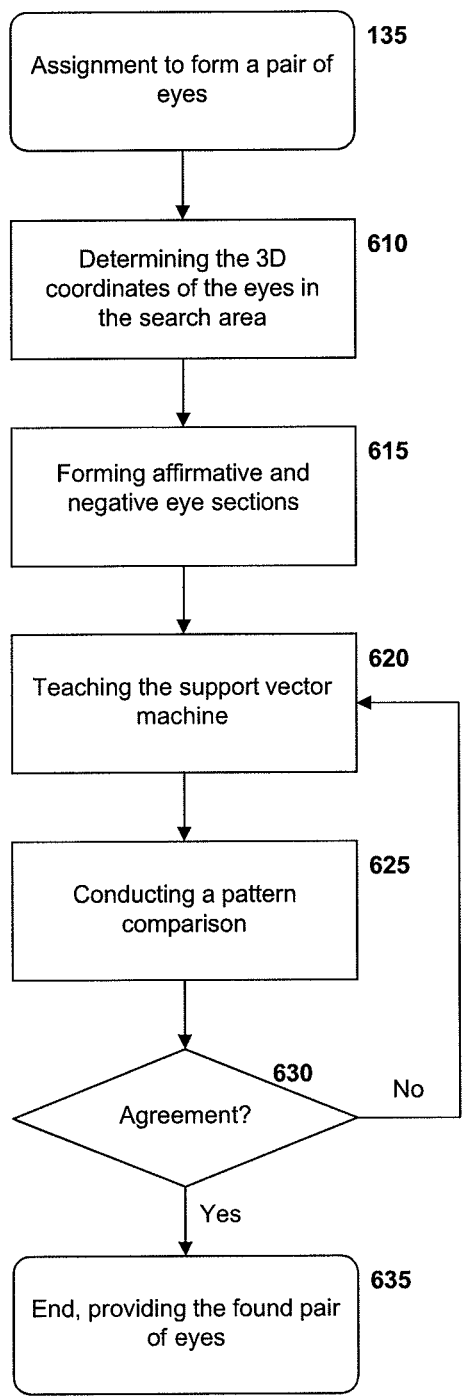
FIG. 6: shows a flowchart that illustrates the process of the assignment of eyes to form pairs of eyes according to an embodiment of this invention.

Further preferred embodiments of the method will now be described with reference to FIG. 6. The process shown in FIG. 6 describes in detail the operations of assigning eyes to form a pair of eyes in step 135 in FIG. 1. The eyes which were detected in the steps of finding and tracking eyes are assigned to form pairs of eyes. First, in step 610 the 3D coordinates of those detected eyes are determined as described above. In a preferred embodiment, the assignment of eyes to form pairs of eyes is carried out by way of a classification. Classification methods are methods and criteria for grouping objects into classes. The classificators known in the prior art can be used as long as they are suitable for assigning objects in image data. In a preferred embodiment, the classificator is a support vector machine. A support vector machine divides a set of objects into classes such that the class boundaries are surrounded by a range free of objects which is as wide as possible. As a prerequisite for this division, the support vector machine is taught with training objects of the sets to be distinguished. In a preferred embodiment a first set of images which show various eyes and a second set of images which show various non-eyes are formed in step 615. These sets are typically formed before the process is executed, but they can also be formed immediately before the step of assigning eyes to form pairs of eyes is executed. The support vector machine is taught with those two sets in step 620 such that a classification of eyes in the image data becomes possible. The found or tracked eyes are then compared by way of a pattern comparison of the support vector machine 625 and will be added either to the class of eyes or to the class of non-eyes, if they exhibit a certain degree of agreement with those classes. The results of the classification can in turn be provided to the support vector machine as training objects. The support vector machine then assigns the eyes to form pairs of eyes, which are then added to the class of eyes. The assignment of eyes to form pairs of eyes according to the just described embodiment ends with step 635 providing assigned pairs of eyes.

Figure 7:
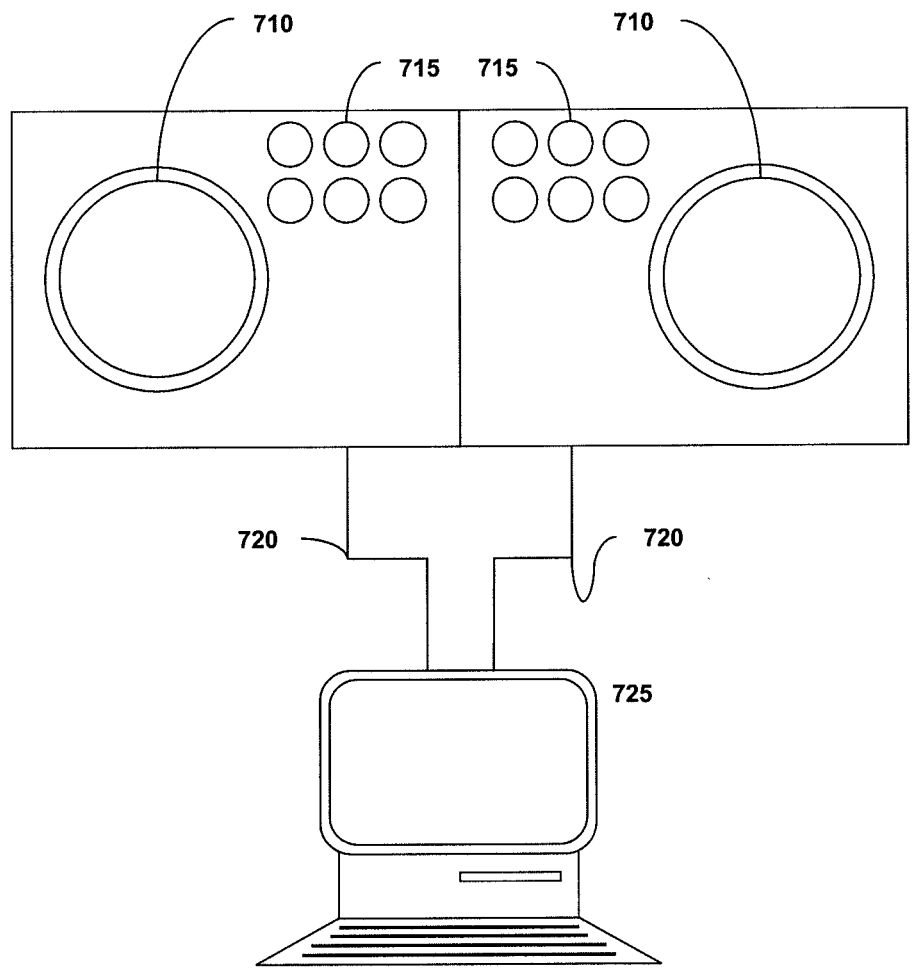
FIG. 7 shows a device according to an embodiment of this invention.

Referring to FIG. 7, a preferred embodiment of a device for finding and subsequent tracking of the 3D coordinates of a pair of eyes in real time will now be described. The drawing shows two image sensors 710 in parallel arrangement, both of which being for example mounted to a common carrier structure, means for an active illumination 715 for each image sensor, and means for transmitting the image data 720 of each image sensor to a central control computer 725, which executes the method according to this invention. In a preferred embodiment, the image sensors 710 are designed in conjunction with the illumination means 715 such that they record image data which represent the 'dark pupil effect'. The image sensors are fitted with non-auto-focussing optical systems for specific detection ranges so that it can be ensured that the used image sensors provide sufficiently sharp image data. Advantageously, image sensors which cover for example a detection range of between 0.5 m and 3.5 m or more, or which cover a smaller range of between 0.5 m and 1.5 m, and/or of between 1.8 m and 3.0 m can be used. The active illumination means 715, which can comprise just one light source according to one embodiment, are preferably designed such to emit pulsed infrared light with a wavelength of approx. 850 nm. The arrangement of the active illumination in relation to the image sensors is determined by the spatial position of the subjects to be found and tracked in relation to the image sensors. The control computer 725 controls the recording of image data by the image sensors through the means for transmitting the image data 720 of each image sensor, where the active illumination is also turned on and off through these transmission means. According to one embodiment, the means for transmitting the image data 720 of each image sensor are implemented in the form of a single serial interface.

In another preferred embodiment, the synchronous control of the image sensors and the active illumination is for example implemented in the form of a clock pulse generator. The images recorded by the image sensors are transmitted to the central control computer 725 through transmission means 720. Currently commercially available hardware components of the control computer 725 allow the method according to this invention for finding and tracking of up to 4 observers to be executed at a detection and tracking frequency of 25 and more images per second. The used hardware components are so compact that they can for example be integrated into the case of a monitor. The eyes which are found and tracked by the control computer 725 can be transmitted through another interface (not shown) for further usage. In a preferred embodiment, both the means for transmitting the image data 720 and the further interface are implemented in the form of serial interfaces. In a preferred embodiment, the device is designed to execute the method in real time, i.e. to find and track eyes in each image which corresponds with the currently received image data.

Figure 8:
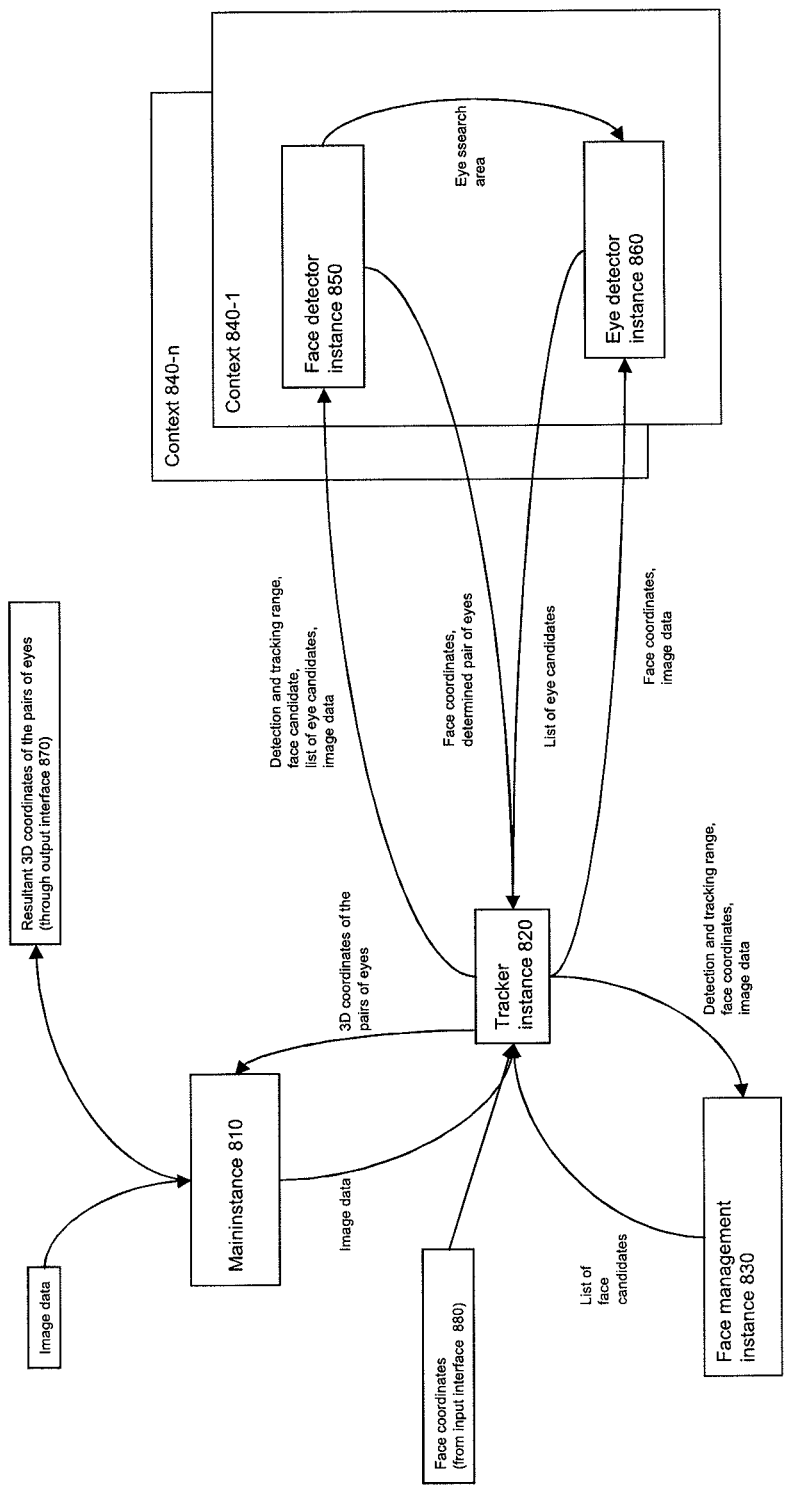
FIG. 8: shows a process flowchart of a computer programme in object-oriented design according to an embodiment of this invention.

The method according to this invention is further preferably implemented in the form of an executable computer programme that controls a computer such as the control computer 725. A preferred embodiment in the form of a computer programme will now be described with reference to FIG. 8. The embodiment shown in FIG. 8 describes a draft routine of the computer programme according to an object-oriented paradigm, where the draft enables a person skilled in the art to implement the computer programme in an object-oriented manner in an adequate development environment.

The objects and instances introduced below partly implement more than one of the above-described process steps, or combine them in the objects and instances. These objects and instances and the process steps which are executed therein are thus given names which differ from those of the process steps described above; however, this does not mean that the processes as such are different. The embodiment described below shall only be construed as one possible object-oriented physical form of the method according to this invention.

A controlling main instance 810 serves as a main loop and thus as a controlling instance for controlling the process steps or process groups which will be detailed below. The following process steps are represented and implemented in the main instance 810:

Acquisition of image data;
Calling up a tracker instance 820;
Computing the 3D coordinates of the eyes by the tracker instance 820 for all eye positions which are detected as valid eye positions;
Filtering by way of restricting the 3D coordinates in permitted ranges, where the filtering step comprises according to further embodiments a noise filtering and a precomputation or forecasting of a 3D position based on the 3D movement speed of the face, in order to compensate the delay of the system. Advantageously, the 3D position is forecast for 60 ms, because this is a typical system delay. The system delay is understood here to be the time that passes from the reception of the image data to the output of the 3D coordinates of the pairs of eyes;
Transmission of the resultant 3D coordinates through an output interface 870 in order to be able to further process the results accordingly.

The input information comprises image data which are acquired in the form of a sequence of digital video signals by one or multiple image sensors. The output information comprises the 3D coordinates of all pairs of eyes.

Multiple context instances 840-1, ..., 840-*n* are implemented to represent an administrative structure for the coordination and administration of the interplay of face detection 115, eye detection 125 and eye tracking 130. Each context instance 840 is assigned with a face detector instance 850 for finding a face 115, and with an eye detector instance 860 for finding eyes 125 in the corresponding eye search area which is determined by the face detector 850. The eyes found by the eye detector 860 thus belong to the face found by the face detector 850. A context 840 is defined to be free if it is not assigned to a subject, thus being available for tracking a new subject.

The major process steps of a context instance 840 include:
Administration of one instance each of a face detector 850 and of an eye detector 860 per subject;
Referencing of these two instances 850, 860 to one subject for the time of its stay in the permitted detection and tracking range;
Controlled assignment and administration of the contexts 840, where contexts 840 can remain free if less subjects are situated in the detection and tracking range than contexts 840 are available, and where no further subjects can be found and tracked if all contexts 840 are occupied.

Further, the interplay of the individual face detector and eye detector instances 850, 860 within the contexts 840 is coordinated and administered by the tracker instance 820. The major process steps of the tracker instance 820 include:
Initialisation of the two detector objects of face detector 850 and eye detector 860;
Administration of the context instances 840-1, ..., 840-*n*;
Reception of the face coordinates from a face detector 850 and transmission to a face management instance 830;
Assignment of newly found faces to free contexts 840;
Calling up the algorithms for face and eye detector 850, 860 of each occupied context 840;
Computing the 3D coordinates of all pairs of eyes;

The input information comprises the image data, and the output information comprises the 3D coordinates of all pairs of eyes.

Special steps of the tracker instance 820 include:
Checking the input interface 880 whether or not new face coordinates are pending and reading those data and adding them to the list of current face positions;
Calling up the face management instance 830 if at least one context 840 is available;
Checking the face candidates of the face management instance 830 whether or not faces have already been tracked in a context 840 and elimination of the face candidates which are found to be redundant;
Assignment of the remaining faces, which are recognised as new faces, to the face detectors 850 of the free contexts 840;
Iteration over all contexts 840-1, ..., 840-*n* with the steps of:
Calling up the face detector 850;
Calling up the eye detector 860 if the face detector 850 is tracking a face; else the current context 840 is marked free;
If the eye detector 860 is in the search mode and if eye candidates were determined then
Selection of the best eye candidates by the face detector 850;
Switching the eye detector 860 to the tracking mode;
Processing the next occupied context 840 until all contexts 840 are processed.

Face coordinates which have been received by the face detector 850 are analysed by a face management instance 830, which compiles a list of candidates of faces which are recognised as valid faces for tracking based on these coordinates.

The steps of this face management instance 830 include:
Administration of the found faces of the face detector 850;

Compilation of a list of candidates of faces which are recognised as valid faces based on the faces found by the face detector 850;

Computing the distances of the faces from the image data providing image sensor based on disparities in the stereo image.

The input information comprises image data and search area for the face search, and the output information comprises a list of found faces and their coordinates.

As a special function, the face management instance 830 includes the steps of:

If the list of current face positions has changed then:
Analysis of that list;
Computing the distance of valid faces from the image data providing image sensor by way of a stereo analysis and adding the faces which are situated within the detection and tracking range to the list of face candidates.

A face to be tracked is administered by a corresponding face detector instance 850. A face detector 850 is assigned with one face from the list of faces of the face management instance 830. The face will be tracked until it moves out of the detection and tracking range. The steps of the face detector instance 850 include:

Administration of the position of a found face;
Computing the search area for the eye detector 860;
Computing the distance of the face from the image data providing image sensor based on the disparities in the stereo image.
Decision for the best pair of eyes from the list of candidates of possible pairs of eyes of the corresponding eye detector 860;
The input information comprises:
Image data;
Information about a found face;
Search area for face tracking 850;
List of candidates of pairs of eyes;
The output information comprises:
List of found faces and their coordinates;
Search area for the eye detector 860;
Selected pair of eyes.

As a special function, this face detector instance 850 includes the steps of:

If the list of current face positions has changed then:
Updating the face position;
Resetting the found/lost reference counter; where this reference counter serves as a measure for in how many subsequent images an already found face has no longer been detected;
Else, if the list has remained unchanged then:
If the eye detector tracks eyes then:
Computing the face position based on the eye position;
Computing the distance of the face/of the eyes;
Else:
The face was lost and the found/lost reference counter is incremented. However, the face still counts as a found face;
The previous face position will remain stored as long as the found/lost reference counter does not exceed a certain preset value; else the face is considered no longer existing.

The detection and tracking of the eyes is carried out by an eye detector instance 860 which either detects eyes in defined search areas in a search mode or which tracks already found eyes in a tracking mode. Possible pairs of eyes are thus determined, and lists of candidates are compiled based on evaluation criteria.

The steps of the eye detector instance 860 include:
Administration of the position of a found pair of eyes;
Initial search for eyes;
Computing the search areas for tracking;
Tracking the eye position;
Determining the confidence of found eye candidates and compiling prospective candidates;
The input information comprises:
Image data;
Search area for eye search and tracking;
Information about the found face;
The output information comprises:
Pair of eyes and their coordinates.

Special functions of this eye detector instance 860 comprise the steps of:

If the eye detector 860 is in the search mode then:
Determining the eye search area by the face detector 850;
Application of algorithms for detecting the eyes within the eye search area;
Else, if the eye detector 860 is in the tracking mode then:
Computing and forecasting or extrapolation of the new positions of the search area and its size based on the speed of the eye determined with the help of previous eye positions and the distance of the observer from the image data providing image sensor;
Application of algorithms for tracking the eyes within the search area;
If candidates were found then:
Conducting of various tests aiming at determining prospective candidates of pairs of eyes. Tests and criteria include:
Position of the eyes in relation to each other and to the face position;
Eye separation and inclination;
Confidence based on a classification of the brightness pattern in the area of the found position and surrounding positions, where surrounding positions with better confidence will be used later for improving the position accuracy;
Compilation of a list of candidates based on the resultant evaluation criteria;
If the eye detector 860 is in the tracking mode then:
If candidates were determined then:
Selection of the candidate pair which is closest to the forecast eye positions;
Updating the current eye positions as the new result;
Else, if no or no suitable candidates were found then:
Switching the eye detector 860 to the search mode and repetition of the search.

The embodiments of the present invention described above are implemented with the help of suitable hardware and software, as already indicated above, such as a digital signal processing device (DSP) and/or a programmable digital integrated circuit (FPGA) and adequate peripheral devices and control programmes which are advantageously executed on a control computer, such as a suitable personal computer.

According to one embodiment, the claimed computer programme is stored or implemented as a software component, for example in the form of source code stored in a ROM, or as a hardware component, for example as a logic circuit in an ASIC or FPGA. If the computer programme is stored for example as a software component in the memory of the control computer, it is executed by the control computer during operation, which according to one embodiment comprises for example a fast digital signal processor (DSP) for executing the software component.

According to one embodiment, the data carrier is a machine-readable data carrier, such as for example a CD-ROM or a ROM on/in which the computer programme is stored.

The invention claimed is:

1. A method for finding the 3D coordinates of a pair of eyes in at least one face, comprising the following steps:
   a) Reception of image data comprising a sequence of at least one digital video signal from at least one image sensor;
   b) Finding eyes in the image data;
   c) Determining the 3D coordinates of the found eyes;
   d) Assignment to the found eyes to form a pair of eyes; and
   e) Output of the 3D coordinates of the pair of eyes;
where the process of finding eyes in the image data comprises the following steps:
   f) Identification of one or multiple faces in the image data;
   g) Determining the 3D coordinates of at least one identified face;
   h) Definition of a first search area on the identified face; and
   i) Finding at least one eye in the first search area;
wherein the process of finding at least one eye in the first search area comprises the following steps:
   j) Computing an expected size of a part of the eye depending on the distance of the identified face from the image data providing image sensor;
   k) Computing a greyscale value as a threshold for a segmentation in the first search area depending on the distance of the identified face from the image data providing image sensor;
   l) Pre-processing the first search area aiming to improve the contrast;
   m) Segmentation of the first search area after the pre-processing;
   n) Computing one or multiple combined regions in the segmented first search area, where the combined region is a collection of adjacent pixels with at least approximately identical greyscale value;
   o) Determining a size of each computed combined region; and
   p) Comparing the expected size of the part of the eye with the determined size of the combined region, where the combined region represents a found eye if the determined size of the combined region at least approximately corresponds with the expected size of the part of the eye.

2. A method for tracking the 3D coordinates of a pair of eyes in at least one face, comprising the following steps:
   a) Reception of image data comprising a sequence of at least one digital video signal from at least one image sensor;
   b) tracking already found eyes in the image data;
   c) Determining the 3D coordinates of the tracked eyes;
   d) Assignment to the tracked eyes to form a pair of eyes; and
   e) Output of the 3D coordinates of the pair of eyes;
wherein:
   the process of tracking already found eyes in the image data comprises the following steps:
   f) Definition of a search area on the identified face; and
   g) Tracking the eyes of the pair of eyes in the search area; and
the process of tracking the eyes of the pair of eyes in the search area comprises the following steps:
   h) Computing an expected size of a part of the eye depending on the distance of the identified face from the image data providing image sensor;
   i) Determining a minimum greyscale value in the search area;
   j) Iteration over a greyscale value as a threshold in the search area, where the iteration is terminated when at least two eyes are detected, comprising the following steps:
   k) Computing the greyscale value as a threshold for a segmentation in the search area depending on the distance of the identified face from the image data providing image sensor, from the current iteration step, and from the minimum greyscale value;
   l) Segmentation of the search area;
   m) Computing one or multiple combined regions in the segmented search area, where the combined region is a collection of adjacent pixels with at least approximately identical greyscale value;
   n) Determining a size of each computed combined region;
   o) Comparing the expected size of the part of the eye with the determined size of the combined region, where the combined region represents a tracked eye if the determined size of the combined region at least approximately corresponds with the expected size of the part of the eye.

3. The method according to claim 1, wherein the segmentation is a binarisation of each pixel, where the pixels are given the value 1 if they are below the threshold, and where they are given the value 0 if they are above the threshold or, vice versa, where the pixels are given the value 0 if they are below the threshold, and where they are given the value 1 if they are above the threshold.

4. The method according to claim 1, wherein the pre-processing in step l) is a greyscale value histogram equalisation.

5. The method according to claim 1, wherein the combined region is an 8-pixel combined region.

6. The method according to claim 1, wherein the part of the eye comprises the pupil, or the pupil and the iris.

7. The method according to claim 1, wherein the assignment of the found eyes to form a pair of eyes comprises a classification.

8. The method according to claim 7, wherein the classification is conducted by a support vector machine, and wherein the support vector machine is taught with one or multiple images of eyes and/or non-eyes.

9. The method according to claim 1, wherein the identification of one or multiple faces in the image data comprises a comparison of the 3D coordinates of an identified face with the 3D coordinates of a face that has been identified in earlier steps and wherein the distance of the identified face from the image data providing image sensor comprises a computation of the distance of the face based on the 3D coordinates of the face.

10. The method according to claim 1, wherein the determining of the 3D coordinates of a face comprises a stereo analysis of the image data.

11. The method according to claim 1, wherein the face is actively illuminated with infrared light during the recording of the image data.

12. The method according to claim 1, wherein the method finds and tracks a pair of eyes at a distance of approx. 0.5 m to 3.5 m from the image sensors.

13. The method according to claim 1, wherein the first search area has a size of about 50 mm ×50 mm.

14. The method The method according to claim 1, wherein the method runs in real time.

15. A non-transitory computer readable storage medium with an executable program stored thereon which, if run on a computer, execute the method according to claim 1, wherein the found 3D coordinates of a pair of eyes in at least one face are used as tracking information for a display device which directs light towards the eyes of an observer.

16. A device for finding the 3D coordinates of a pair of eyes in at least one face, said device being designed such to be able to execute a method according to claim 1.

17. The method according to claim 2, wherein the segmentation is a binarisation of each pixel, where the pixels are given the value 1 if they are below the threshold, and where they are given the value 0 if they are above the threshold or, vice versa, where the pixels are given the value 0 if they are below the threshold, and where they are given the value 1 if they are above the threshold.

18. The method according to claim 2, wherein the combined region is an 8-pixel combined region.

19. The method according to claim 2, wherein the part of the eye comprises the pupil, or the pupil and the iris.

20. The method according to claim 2, wherein the assignment of the found or tracked eyes to form a pair of eyes comprises a classification.

21. The method according to claim 20, wherein the classification is conducted by a support vector machine, and wherein the support vector machine is taught with one or multiple images of eyes and/or non-eyes.

22. The method according to claim 2, wherein the face is actively illuminated with infrared light during the recording of the image data.

23. The method according to claim 2, wherein the method finds and tracks a pair of eyes at a distance of approx. 0.5 m to 3.5 m from the image sensors.

24. The method according to claim 2, wherein the search area has a size of about 20 mm ×15 mm

25. The method according to claim 2, wherein the method runs in real time.

26. A non-transitory computer readable storage medium with an executable program stored thereon which, if run on a computer, execute the method according to claim 2, wherein the tracked 3D coordinates of a pair of eyes in at least one face are used as tracking information for a display device which directs light towards the eyes of an observer.

* * * * *